United States Patent [19]

Mitchell et al.

[11] Patent Number: 4,782,159

[45] Date of Patent: Nov. 1, 1988

[54] PROCESS FOR PREPARING BETA-METHYL-GAMMA-OXO-4-(4-OXO-1(4H)-PYRIDINYL) DERIVATIVE OF BENZENE BUTANOIC ACID

[75] Inventors: Michael B. Mitchell, Hildenborough; Kiritkant D. Pancholi, Welwyn Garden City, both of England

[73] Assignee: Smith Kline & French Laboratories Limited, Welwyn Garden City, England

[21] Appl. No.: 149,782

[22] Filed: Jan. 29, 1988

Related U.S. Application Data

[63] Continuation-in-part of Ser. No. 094,627, Sep. 9, 1987, abandoned.

[30] Foreign Application Priority Data

Sep. 11, 1986 [GB] United Kingdom ............... 8621864

[51] Int. Cl.$^4$ .......................................... C07D 211/86
[52] U.S. Cl. ..................................... 546/301; 544/238
[58] Field of Search ............................... 546/301, 302

[56] References Cited

U.S. PATENT DOCUMENTS 4,731,371 3/1988 Jones et al. .......................... 514/336
4,732,982 3/1988 Jones et al. .......................... 546/261

Primary Examiner—Alan L. Rotman
Attorney, Agent, or Firm—Linda E. Hall; Janice E. Williams; Alan D. Lourie

[57] ABSTRACT

A process for the prepartion of 3-[4-(4-oxo-1,4-dihydropyridin-1-yl)benzoyl]butanoic acid which comprises the reaction of 3-(4-fluorobenzoyl)butanoic acid with 4-hydroxypyridine under aqueous conditions in the presence of a base.

8 Claims, No Drawings

PROCESS FOR PREPARING BETA-METHYL-GAMMA-OXO-4-(4-OXO-1(4H)-PYRIDINYL) DERIVATIVE OF BENZENE BUTANOIC ACID

This application is a continuation-in-part of U.S. patent application No. 094,627 filed Sept. 9, 1987, now abandoned.

The present invention relates to a process for preparing N-phenylpyridone derivatives. Specifically this invention relates to a process for preparing the compound of the formula (1) which is a useful intermediate in the preparation of the compound of the formula (2):

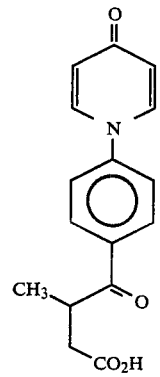

(1)

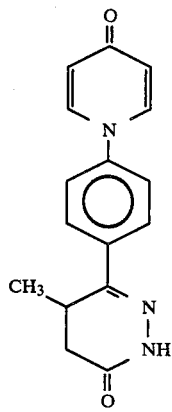

(2)

The compound of the formula (2) is a selective phosphodiesterase type III inhibitor with positive inotropic and vasodilator activity as described in the following in vivo and in vitro tests:

Cardiac Stimulant Activity—In vivo (Anaesthetised Cats)

In anaesthetised cats pretreated with a ganglion blocker (mecamylamine or pempidine) and propranolol, the compound of formula (2) causes increases in left ventricular dp/dt max (this is an index of left ventricular contractility) when administered intravenously. The dose to increase left ventricular dp/dt max by 50% is given as the $ED_{50}$. The compound of formula (2) had an $ED_{50}$ of 0.04 micromole/kg. Amrinone had an $ED_{50}$ of 5.6 micromole/kg. Minimal changes in blood pressure or heart rate were observed.

Cardiac Stimulant Activity—In vivo (Conscious Dogs)

The compound of formula (2) increased left ventricular dp/dt max in conscious dogs after intravenous administration at doses below 0.02 mg/kg. Oral administration caused positive inotropic responses at doses of 0.05 mg/kg and below. These positive inotropic responses persisted for more than 3 hours (maximum duration of measurement) without changes in blood pressure or heart rate. Therefore this compound is particularly beneficial with regard to 'force-rate' selectivity. In contrast amrinone is less active and is of shorter duration.

Inhibition of Phosphodiesterases

Three peaks of cyclic nucleotide phosphodiesterase activity [PDE (Peak I), PDE (Peak II) and PDE (Peak III)] from cat heart were separated by chromatography on DEAE Sepharose CL-6B (Diethylaminoethyl Cellulose with a bead size of 45–165 microns). Sepharose is a registered trademark of Pharmacia Fine Chemicals Inc. The high-speed supernatant from a cat heart homogenate (2 g tissue in 20 ml 20 mM PIPES (Piperazine-N-N'-bis[2-ethanesulfonic acid]), 50 mM Na acetate, pH 6.5) was applied to a 15×1.5 cm column of DEAE-Sepharose equilibrated with the homogenisation buffer. The PDE activities were eluted with a gradient of 0.05–1M Na acetate in 20 mM PIPES. There were three major peaks which had the following characteristics:

| PDE (Peak I) - eluted at 0.15 M Na acetate | | | |
|---|---|---|---|
| Substrate | 50 μg/ml calmodulin (+ = added) | Km (μM) | Relative $V_{max}$ |
| cyclic AMP | − | 0.5 | 1 |
| cyclic GMP | − | 1.8 | 1.1 |
| cyclic AMP | + | 0.7 | 6.3 |
| cyclic GMP | + | 1.4 | 7.2 |

| PDE (Peak II) - eluted at 0.3 M Na acetate | | |
|---|---|---|
| Substrate | Km (μM) | Relative $V_{max}$ |
| cyclic AMP | 6 | 1 |
| cyclic GMP | 28 | 0.2 |

| PDE (Peak III) - eluted at 0.5 M Na acetate | | |
|---|---|---|
| Substrate | Km (μM) | Relative $V_{max}$ |
| cyclic AMP | 0.6 | 1 |
| cyclic GMP | 2.9 | 0.4 |

PDE (Peak I) has high affinity for cyclic AMP and cyclic GMP and is characterized by an activation by $Ca^{2+}$/calmodulin complex.

PDE (Peak II) demonstrates relatively low affinities for both cyclic AMP and cyclic GMP and is not affected by $Ca^{2+}$/calmodulin complex.

PDE (Peak III) has high affinity for cyclic AMP. It can also hydrolyse cyclic GMP though the preferred substrate is cyclic AMP. This activity is also insensitive to $Ca^{2+}$/calmodulin activation.

Enzyme assay

The enzyme was assayed by incubation at 37° for 4–30 min in 50 mM Tris, 5 mM $MgCl_2$, pH 7.5 with [3-H] cyclic nucleotide ($4 \times 10^5$ disintegrations $min^{-1}$) and [14-C] nucleotide 5' monophosphate ($3 \times 10^3$ disintegrations $min^{-1}$). The assay was stopped by boiling, and the [3-H] 5'monophosphate product separated from substrate on boronate columns (Davis, C. W. and Daly, J. W. (1979) J. Cyclic Nucleotide Res., 5, 65–74). The reaction mixture was diluted with 0.5 ml 100 mM HEPES (N-2-Hydroxyethylpiperazine-N'-2-ethanesulfonic acid), 100 mM NaCl, pH 8.5, and applied to the column. The column was extensively washed with the same buffer, and the 5' nucleotide eluted with 6 ml 0.25M acetic acid. The recovery of product as judged by [14-C] recovery was approximately 80%. All assays were linear with time of incubation and concentration of enzyme over the range used in these experiments.

Calculation of $IC_{50}$ values $IC_{50}$ values (the concentration of inhibitor required for 50% inhibition of activity) were obtained for PDE (Peak III) by incubation of the enzyme at 1 μM cyclic AMP, and a range of inhibitor concentration from $0.1 \times IC_{50}$ to $100 \times IC_{50}$.

| Compound | $IC_{50} \times 10^{-6}$ M |
|---|---|
| formula (2) | 0.41 |
| Amrinone | 51.8 |
| Milrinone | 2.2 |

Specificity

The compound of formula (2) showed no inhibition at up to $10^{-4}$M when incubated with PDE (Peak I) and either no or weak inhibition with respect to PDE (Peak II) i.e. it is a selective PDE (Peak III) inhibitor. This specificity is an indication that the compound is likely to have a force/rate selectivity in its cardiac stimulant activity with a low potential for inducing arrythmias.

Vasodilator Activity

The compound of formula (2) was tested in autoperfused anaesthetised cat hindquarters (autoperfused at constant blood flow). The i.v. dose to decrease hindquarters perfusion pressure (vasodilatation) by 15% is given as $ED_{15}$. The compound of formula (2) had an $ED_{15}$ of 0.05 μm/kg.

Bronchodilatation—In vivo

Male guinea-pigs of the Dunkin Hartley strain (530 g±6 g) were anaesthetised with Sagatal (pentobarbital sodium) (90 mg/kg i.p.). Airway resistance was measured using a modification of the classical Konzett-Rossler technique (Versuchsanordnung zu Untersuchungen an der Bronchialmuskulatur. Naunyn-Schmiedebergs Arch. Exp. Path. Pharmak., 195: pp 71-74, (1940)). A dose of histamine which gave approximately 150% increase in airway resistance was selected for i.v. administration. Bolus doses of the compound of formula (2) was administered (i.v.) one minute before the histamine challenge.

The compound of formula (2) reduced the histamine-induced bronchoconstriction. The threshold dose for this compound was $1 \times 10^{-8}$ mol/kg. The dose of the compound of formula 2 which reduced the histamine bronchoconstriction by 50% ($ED_{50}$) was $1.8 \times 10^{-6}$ mol/kg, demonstrating in-vivo anti-bronchoconstrictor activity.

Platelet Aggregation Inhibition—In vitro

Platelet rich plasma (PRP) was prepared from whole human blood anti-coagulated with 1/10 volume acid citrate dextrose. The citrated blood was centrifuged at 700 g for 5 minutes and the PRP removed. The remaining red cells and plasma were centrifuged for a further 15 minutes at 900 g and the platelet poor plasma removed. This was then mixed with the PRP to give a final platelet count of $2-3 \times 10^8$ cells/ml.

PRP was divided into 0.5 ml aliquots which were preincubated for 2 minutes to 37° C. before being placed in the sample chamber of an HG aggregometer connected to a Teckman chart recorder.

Aspirin was added to a concentration of 100 μM.

Aggregation to the endoperoxide mimetic U44069 (9,11-epoxymethano-$PGH_2$) was then examined in the absence and presence of a range of concentrations of the compound of formula (2).

The compound of formula (2) inhibited aggregation induced by the endoperoxide mimetic U44069 (10 μM) in asprin-treated platelet rich plasma with an $IC_{50}$ value of 0.08±0.01 μM.

A suitable preparation of the compound of the formula (1) is to treat a compound of the formula (3) with 4-hydroxypyridine.

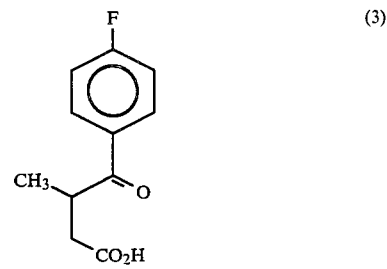

(3)

In the literature similar nucleophilic aromatic substitutions have been performed in the presence of strong bases in dipolar aprotic solvents under anhydrous conditions. For example in J. Med. Chem. 1985 28, 1405-1413 a compound of the formula (4) is prepared by reacting a compound of the formula (5) with imidazole in the presence of 2 molar equivalents of sodium hydride in a mixture of dimethylsulphoxide and toluene at 100°-110° C. for 18 hours.

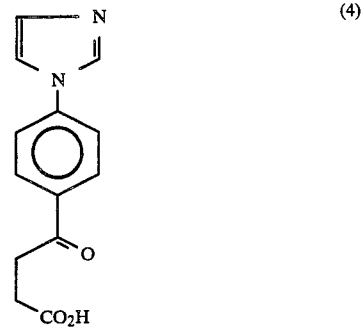

(4)

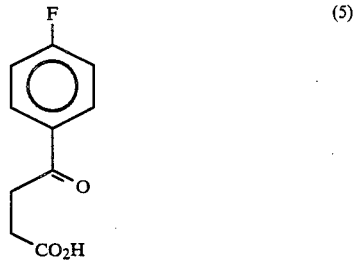

(5)

We have prepared the compound of the formula (1) by reacting the sodium derivatives of a compound of the formula (3) with the sodium derivative of 4-hydroxypyridine in N-methylpyrrolidin-2-one at 105° C. for 4½ hours. The sodium derivatives were separately formed by treatment with sodium hydride in N-methylpyrrolidin-2-one. In order to isolate the product the cooled reaction mixture was poured into water, the resultant mixture was acidified to pH 4 with dilute hydrochloric acid and then extracted with dichloromethane. Evaporation of the organic extract gave the compound of the formula (1) in 40% yield. Extraction of the remaining aqueous mixture with n-butanol and evaporation of the organic extract gave less pure product in 26% yield. Although this process affords the compound of the formula (1) in an overall yield of 66% the product required further purification and the inefficient extraction procedure involving n-butanol is unattractive on a commercial scale.

We have attempted to avoid the use of dipolar aprotic solvents and to prepare the compound of the formula (1) by reacting a compound of the formula (3) with 4-hydroxypyridine in ethanol under reflux in the presence of sodium ethoxide. Under these conditions the reaction is slow and leads to the formation of compounds of the formulae (1) and (6) in approximately equal amounts.

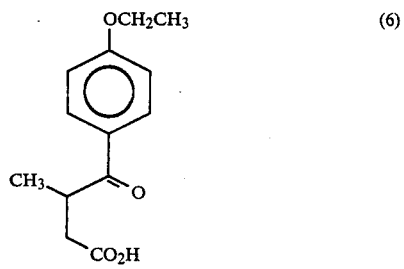

(6)

Surprisingly, we have now found that a compound of the formula (1) can be prepared from a compound of the formula (3) in very good yield under conditions which are particularly suitable for commercial manufacture on the plant scale.

Accordingly the present invention provides a process for preparing a compound of the formula (1) which comprises reacting a compound of the formula (3) with 4-hydroxypyridine characterized in that the process is performed under aqueous conditions in the presence of a suitable base.

Suitably an excess of 4-hydroxypyridine is used in the reaction. Preferably between 1 to 4 moles, particularly 1.5 to 3 moles, of 4-hydroxypyridine are used for each mole of a compound of the formula (3).

By a suitable base we mean a base which will abstract the acidic protons of 4-hydroxypyridine and a compound of the formula (3) under aqueous conditions. Examples of such bases include alkali metal hydroxides such as sodium and potassium hydroxide, alkaline earth metal hydroxides such as calcium hydroxide or organic bases such as tetramethylguanidine or 1,8-diazabicyclo[5.4.0]undec-7-ene. Preferably a sufficient quantity of an alkali metal hydroxide is used to form the anions of 4-hydroxypyridine and the compound of the formula (3). Thus if 1 mole of a compound of the formula (3) is used with 2 moles of 4-hydroxypyridine, then preferably at least 3 moles of sodium hydroxide are used. Suitably an excess of an alkali metal hydroxide is used in the reaction. Suitably the reaction is performed within a pH range of 9 to 14.

Suitably the reaction is performed at a elevated temperature, for example at the reflux temperature of the reaction mixture. Suitably the reaction is performed in an autoclave within the temperature range 100°–200° C., for example at about 140° C.

Preferably the reaction is performed at a reasonable concentration, for example 2 moles of a compound of formula (3) per liter of solvent.

The product is conveniently precipitated in high yield and high purity from the cooled reaction mixture on acidification to pH 3–4 with a mineral acid such as hydrochloric acid.

This process not only avoids the use of expensive and inflammable organic solvents and bases such as sodium hydride but has the advantage that the product can be readily isolated from the reaction mixture on acidification without recourse to a laborious and inefficient solvent extraction process.

Organic solvents such as alcohols e.g. isopropanol or n-butanol can be added to the reaction mixture, however since isolation of the product would be more complicated involving evaporation of the organic solvent followed by acidification of the residue, preferably the reaction is performed in the absence of an organic co-solvent.

This invention is illustrated by the following Examples.

EXAMPLE 1

A solution of 3-(4-fluorobenzoyl)butanoic acid (8 g), 4-hydroxypyridine (8 g) and sodium hydroxide (4.6 g) in water (80 ml) was heated in an autoclave at 140° C. for 20 hours. The reaction mixture was cooled and was acidified to pH 3–4 with dilute hydrochloric acid to afford as a white crystalline precipitate 3-[4-(4-oxo-1,4-dihydropyridin-1-yl)benzoyl]butanoic acid, 9.45 g (87%), m.p. 250°–252° C.

EXAMPLE 2

A solution of 3-(4-fluorobenzoyl)butanoic acid (885 g), 4-hydroxypyridine (663 g) and sodium hydroxide (453 g) in water (2.2 liters) was stirred under reflux for 24 hours. The reaction mixture was cooled, diluted with water (10 liters) and filtered through diatomaceous earth. The filtrate was acidified to pH 3 with concentrated hydrochloric acid to afford as a cream solid 3-[4-(4-oxo-1,4-dihydropyridin-1-yl)benzoyl]butanoic acid, 1127 g (94%), m.p. 251°–254° C.

What is claimed is:

1. A process for preparing a compound of the formula (1):

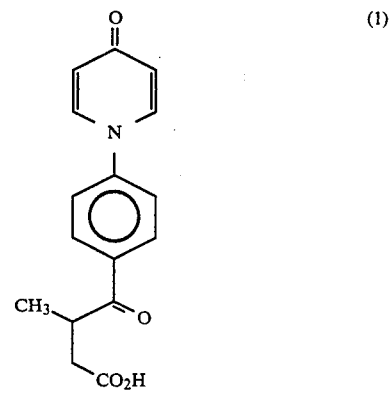

(1)

which comprises reacting a compound of the formula (3):

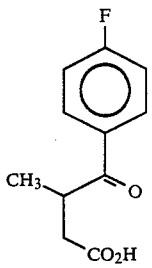

with 4-hydroxypyridine wherein the process is performed under aqueous conditions in the presence of a suitable base.

2. A process according to claim 1 wherein from 1 to 4 mole equivalents of 4-hydroxypyridine are used for each mole equivalents of a compound of the formula (3).

3. A process according to claim 1 wherein a suitable base is an alkali metal hydroxide or alkaline earth metal hydroxide.

4. A process according to claim 3 wherein sufficient alkali metal hydroxide is used to form the anions of a compound of the formula (3) and 4-hydroxypyridine.

5. A process according to claim 4 wherein the alkali metal hydroxide is sodium hydroxide.

6. A process according to claim 1 wherein the reaction is performed in the absence of an organic co-solvent.

7. A process according to claim 6 wherein the product is isolated by adjustment to pH 3-4 with a mineral acid.

8. A process according to claim 7 wherein the mineral acid is hydrochloric acid.

* * * * *